(12) United States Patent
Martinez (10) Patent No.: US 11,590,036 B2
(45) Date of Patent: Feb. 28, 2023

(54) FEMININE HYGIENE PRODUCT ASSEMBLY

(71) Applicant: Nancy Martinez, Torrance, CA (US)

(72) Inventor: Nancy Martinez, Torrance, CA (US)

( * ) Notice: Subject to any disclaimer, the term of this patent is extended or adjusted under 35 U.S.C. 154(b) by 1022 days.

(21) Appl. No.: 16/351,671

(22) Filed: Mar. 13, 2019

(65) Prior Publication Data

US 2020/0289344 A1    Sep. 17, 2020

(51) Int. Cl.
| | | |
|---|---|---|
| *A61F 13/551* | (2006.01) | |
| *A61F 13/20* | (2006.01) | |
| *A61F 13/472* | (2006.01) | |
| *A45C 11/00* | (2006.01) | |
| *A45C 13/10* | (2006.01) | |
| *A45F 3/02* | (2006.01) | |
| *A45F 3/00* | (2006.01) | |
| *A61F 13/47* | (2006.01) | |
| *A61F 13/84* | (2006.01) | |

(52) U.S. Cl.
CPC ........ *A61F 13/5519* (2013.01); *A45C 11/008* (2013.01); *A45C 13/103* (2013.01); *A45F 3/02* (2013.01); *A61F 13/202* (2013.01); *A61F 13/472* (2013.01); *A61F 13/55145* (2013.01); *A61F 13/55175* (2013.01); *A45C 2011/007* (2013.01); *A45C 2200/10* (2013.01); *A45F 2003/003* (2013.01); *A61F 2013/4708* (2013.01); *A61F 2013/8497* (2013.01)

(58) Field of Classification Search
CPC .......... A61F 13/55145; A61F 13/55175; A61F 13/5519; A45C 5/005

USPC ................................... 206/363, 438, 440
See application file for complete search history.

(56) References Cited

U.S. PATENT DOCUMENTS

| | | | | |
|---|---|---|---|---|
| 5,579,916 A | * | 12/1996 | Manko ............... | A61F 15/001 206/440 |
| 7,104,977 B2 | | 9/2006 | Price | |
| 7,144,391 B1 | * | 12/2006 | Kreutz ............... | A61F 13/515 604/385.18 |
| D782,815 S | | 4/2017 | Hernandez | |
| 2003/0136704 A1 | * | 7/2003 | Burgess ............. | A61F 13/82 206/440 |
| 2005/0115855 A1 | * | 6/2005 | Hilel ................ | A45C 11/008 206/440 |
| 2006/0266663 A1 | | 11/2006 | Rhea | |
| 2010/0000897 A1 | * | 1/2010 | Bumpass ........... | A61F 13/26 206/440 |
| 2011/0215025 A1 | | 9/2011 | Gonzales | |

FOREIGN PATENT DOCUMENTS

WO         WO0217844         3/2002

* cited by examiner

*Primary Examiner* — Catharine L Anderson (57) ABSTRACT

A feminine hygiene product assembly for fulfilling feminine hygiene requirements away from a home of a user includes a master kit, which in turn comprises a plurality of subkits. Each subkit comprises a plurality of hygienic products, such as tampons, compact tampons, sanitary napkins, panty liners, sanitary wipes, analgesic capsules, and analgesic tablets. Each hygienic product is positioned in an associated bag and has a respective function so that each subkit comprises hygienic products that have a variety of functions. The master kit is configured to provide a user a respective subkit to address associated hygiene requirements of the user.

18 Claims, 6 Drawing Sheets

FEMININE HYGIENE PRODUCT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to feminine hygiene products and more particularly pertains to a new assembly of feminine hygiene products for fulfilling feminine hygiene requirements away from a home of a user.

BRIEF SUMMARY OF THE INVENTION

An embodiment of the disclosure meets the needs presented above by generally comprising a master kit, which in turn comprises a plurality of subkits. Each subkit comprises a plurality of hygienic products, such as tampons, compact tampons, sanitary napkins, panty liners, sanitary wipes, analgesic capsules, and analgesic tablets. Each hygienic product is positioned in an associated bag and has a respective function so that each subkit comprises hygienic products that have a variety of functions. The master kit is configured to provide a user a respective subkit to address associated hygienic requirements of the user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 8 thereof, a new feminine hygiene products embodying the principles and concepts of an embodiment of the disclosure and generally designated by the reference numeral 10 will be described.

Figure 1:
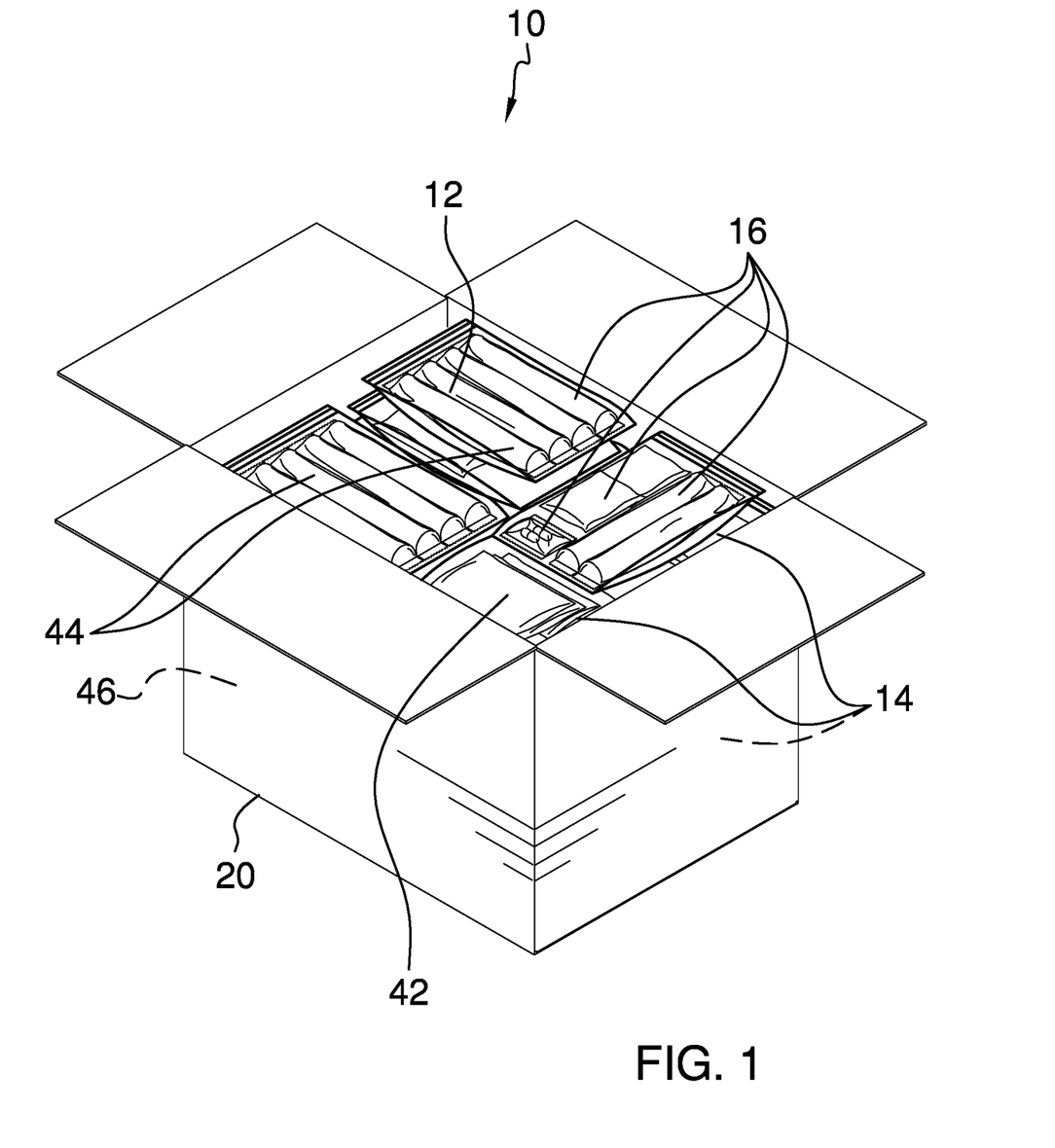
FIG. 1 is an isometric perspective view of a feminine hygiene product assembly according to an embodiment of the disclosure.

As best illustrated in FIGS. 1 through 8, the feminine hygiene product assembly 10 generally comprises a master kit 12, which in turn comprises a plurality of subkits 14. Each subkit 14 comprises a plurality of hygienic products 16, each of which is positioned in an associated bag 18. Each hygienic product 16 has a respective function so that each subkit 14 comprises hygienic products 16 that have variety of functions. The master kit 12 is configured to provide a user a respective subkit 14 to address associated hygienic requirements of the user. The assembly 10 also comprises a box 20, as shown in FIG. 1, that is configured to stow the master kit 12. The master kit 12 is particularly useful in addressing the hygienic requirements of a user who will not have access to hygienic products 16 for an extended period of time, such as a user who is in the military and subject to extended deployment.

Figure 2:
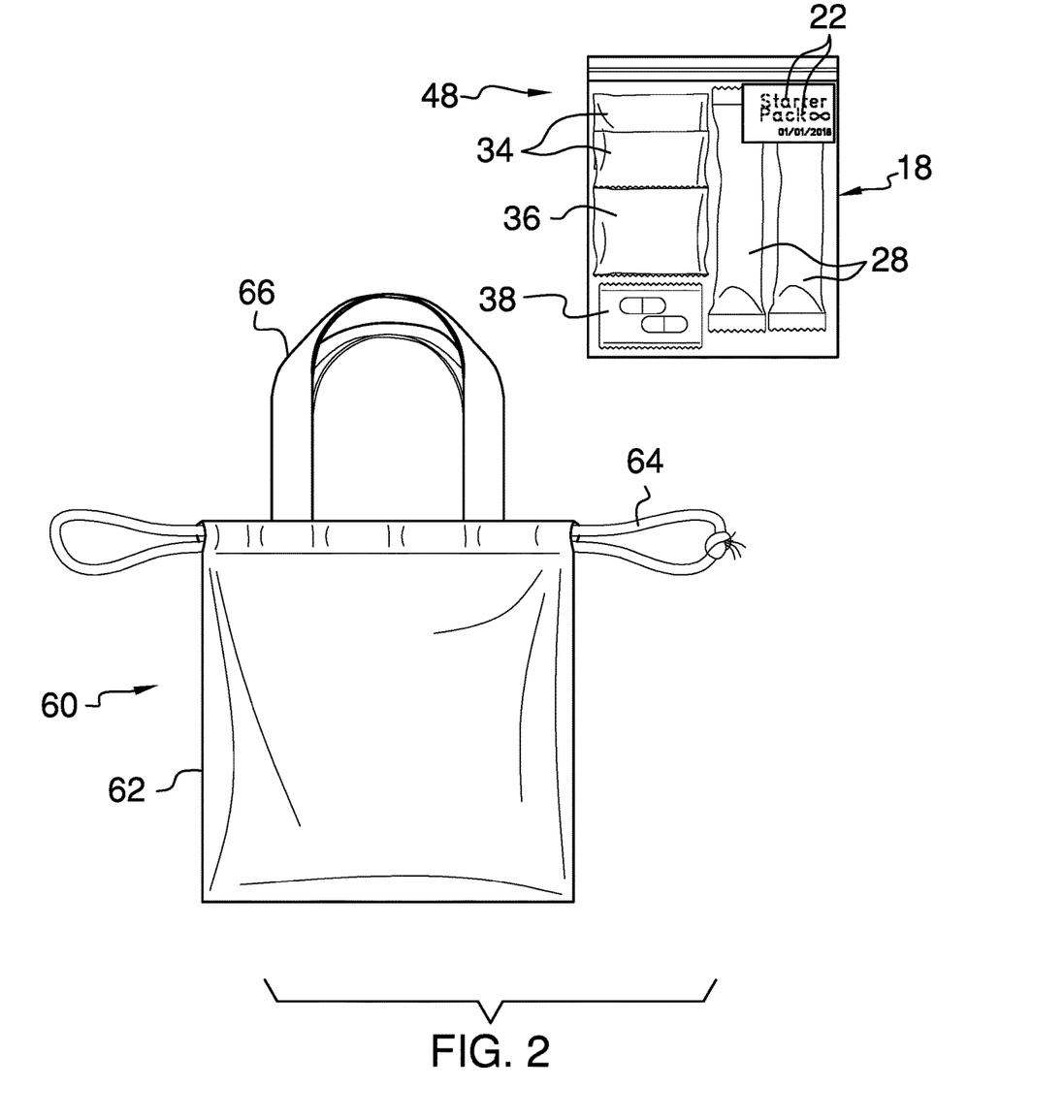
FIG. 2 is a front view of an embodiment of the disclosure.

The associated bag 18 is re-sealable zipper storage type, as shown in FIG. 2. The associated bag 18 is substantially transparent so that the hygienic product 16 is viewable through the associated bag 18. Respective kit indicia 22 of a plurality of kit indicia 22 are coupled to a respective bag 18 to identify an associated subkit 14 that is positioned in the respective bag 18, as shown in FIGS. 2-4 and 7. The respective kit indicia 22 that are coupled to the respective bag 18 comprises a date.

Each hygienic product 16 is sealably contained within a respective sleeve 24 of a plurality of sleeves 24 to maintain sterility of the hygienic product 16. The respective sleeve 24 may be substantially transparent so that the hygienic product 16 is viewable through the respective sleeve 24. Respective product indicia 26 of a plurality of product indicia 26 are coupled to a respective sleeve 24, as shown in FIG. 2, to identify an associated hygienic product 16 that is positioned in the respective sleeve 24.

Each subkit 14 comprises at least one of a plurality of tampons 28, a plurality of compact tampons 30, a plurality of sanitary napkins 32, a plurality of panty liners 34, a plurality of sanitary wipes 36, a plurality of analgesic capsules 38, and a plurality of analgesic tablets 40.

The plurality of subkits 14 comprises a plurality of maxicare kits 42, as shown in FIG. 1. Each maxicare kit 42 comprises a plurality of sanitary napkins 32. Each sanitary napkin 32 has a respective absorbency so that the maxicare kit 42 comprises sanitary napkins 32 that have a variety of absorbencies. The maxicare kit 42 comprises three sanitary napkins 32 individually configured for light, regular, and overnight menstruation.

The plurality of subkits 14 also comprises a plurality of tampon kits 44, examples of which are shown in FIG. 1. Each tampon kit 44 comprises a plurality of tampons 28. Each tampon 28 has a respective absorbency so that the tampon kit 44 comprises tampons 28 that have a variety of absorbencies. The tampon kit 44 comprises one each of tampons 28 that are rated for light absorbency, regular absorbency, super absorbency, and super plus absorbency.

The plurality of subkits 14 also comprises a plurality of compact tampon kits 46, not shown. Each compact tampon kit 44 comprises a plurality of compact tampons 30. Each compact tampon 30 has a respective absorbency so that the compact tampon kit 44 comprises compact tampons 30 that have a variety of absorbencies. The compact tampon kit 44 comprises one each of compact tampons 30 that are rated for light absorbency, regular absorbency, super absorbency, and super plus absorbency.

The plurality of subkits 14 also comprises a plurality of starter kits 48, an example of which is shown in FIG. 2. Each starter kit 48 comprises a plurality of tampons 28, a plurality of panty liners 34, a plurality of sanitary wipes 36, and at least one of a plurality of analgesic capsules 38 and a plurality of analgesic tablets 40. The starter kit 48 comprises two tampons 28 that are rated for light absorbency, two panty liners 34, one sanitary wipe 36, and at least one of a pair of analgesic capsules 38 and a pair of analgesic tablets 40.

Figure 3:
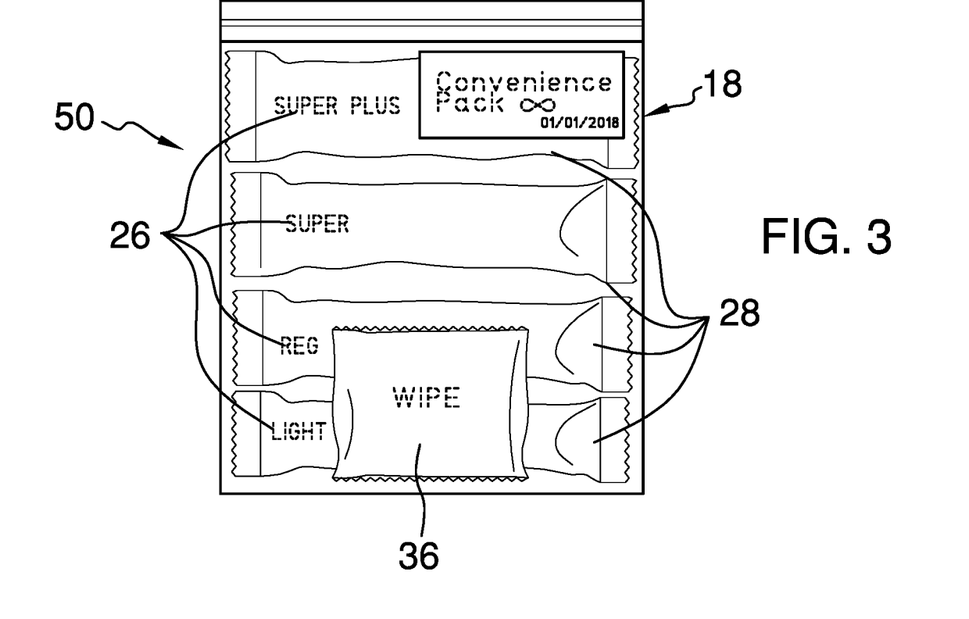
FIG. 3 is a front view of an embodiment of the disclosure.
Figure 4:
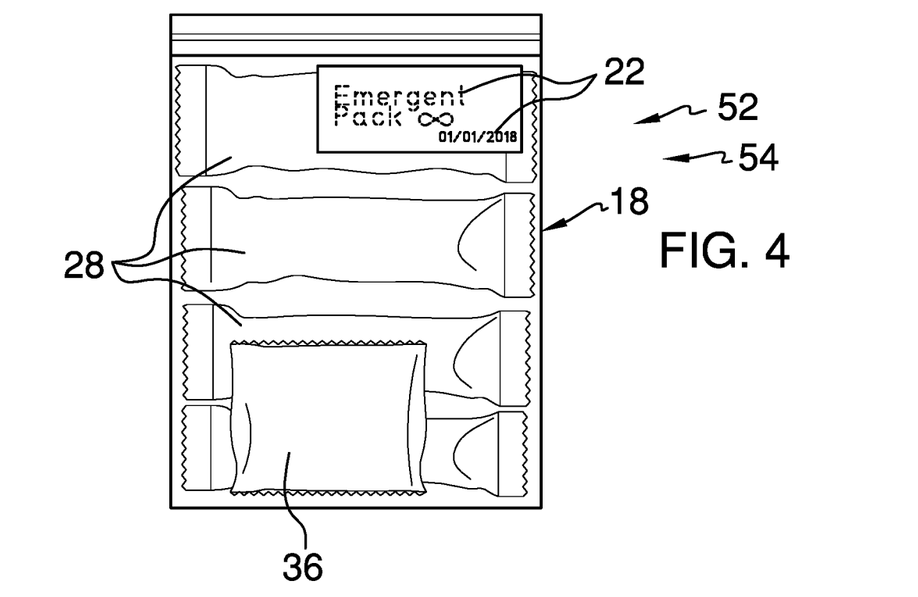
FIG. 4 is a front view of an embodiment of the disclosure.

The plurality of subkits 14 also comprises a plurality of convenience kits 50, an example of which is shown in FIG. 3. Each convenience kit 50 comprises a plurality of tampons 28 and plurality of sanitary wipes 36. The convenience kit 50 comprises one each of tampons 28 that are rated for light absorbency, regular absorbency, super absorbency, and super plus absorbency, and one sanitary wipe 36.

The plurality of subkits 14 also comprises a plurality of regular sized emergent kits 52, an example of which is shown in FIG. 3. Each regular sized emergent kit 52 comprises a plurality of tampons 28 and plurality of sanitary wipes 36. The regular sized emergent kit 52 comprises one each of tampons 28 that are rated for light absorbency, regular absorbency, super absorbency, and super plus absorbency, and one sanitary wipe 36.

The plurality of subkits 14 also comprises a plurality of compact sized emergent kits 54, not shown. Each compact sized emergent kit 54 comprises a plurality of compact tampons 30 and plurality of sanitary wipes 36. The compact sized emergent kit 54 comprises one each of compact tampons 30 that are rated for light absorbency, regular absorbency, super absorbency, and super plus absorbency, and one sanitary wipe 36.

Figure 7:
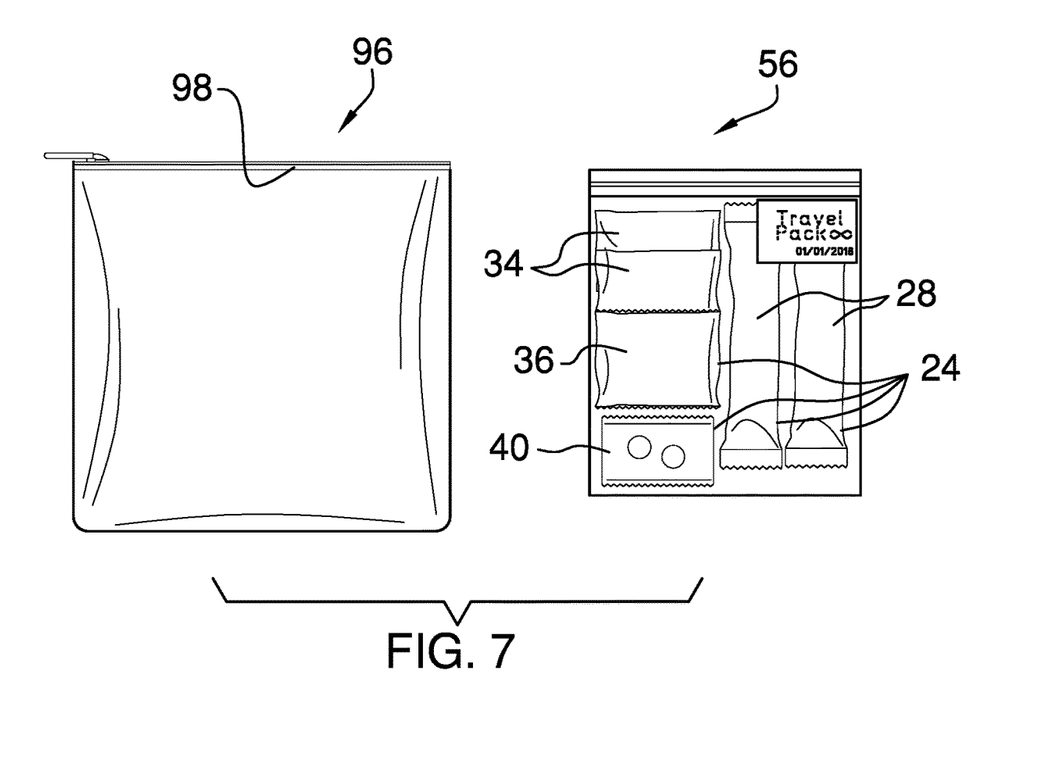
FIG. 7 is a front view of an embodiment of the disclosure.
Figure 8:
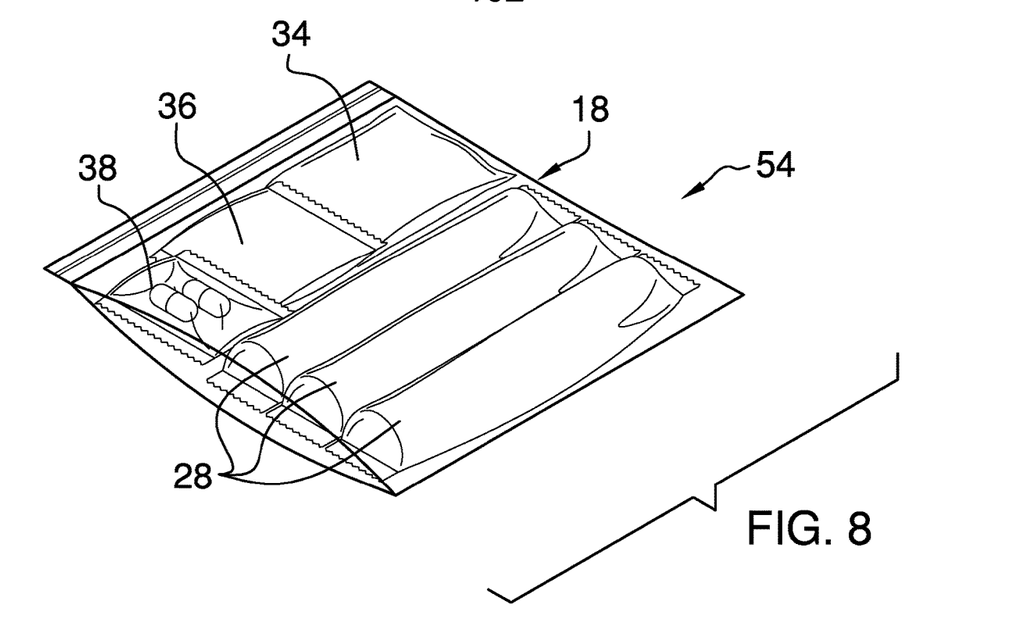
FIG. 8 is an isometric perspective view of an embodiment of the disclosure.

The plurality of subkits 14 also comprises a plurality of travel kits 56 an example of which is shown in FIG. 7. Each travel kit 56 comprises a plurality of tampons 28, a plurality of sanitary napkins 32, a plurality of sanitary wipes 36, and at least one of a plurality of analgesic capsules 38 and a plurality of analgesic tablets 40. The travel kit 56 comprises two tampons 28, two sanitary napkins 32, one sanitary wipe 36, and at least one of a pair of analgesic capsules 38 and a pair of analgesic tablets 40.

The plurality of subkits 14 also comprises a plurality of compact kits 58. Each compact kit 58 comprises a plurality of compact tampons 30, a plurality of panty liners 34, a plurality of sanitary wipes 36, and at least one of a plurality of analgesic capsules 38 and a plurality of analgesic tablets 40. The compact kit 58 comprises three compact tampons 30, one panty liner 34, and at least one of a pair of analgesic capsules 38 and a pair of analgesic tablets 40.

The assembly 10 also comprises a starter pouch 60, as shown in FIG. 7, that is sized complementarily to the starter kit 48 so that the starter pouch 60 is positioned to insert the starter kit 48. The starter pouch 60 comprises a sack 62 with a cinch closure 64 and a handle 66, positioning the user to enclose the starter kit 48 within the sack 62 and to carry the sack 62 by the handle 66.

The assembly 10 also comprises a car kit 68, not shown, which in turn comprises at least one of the maxicare kits 42, the tampon kits 44, the compact tampon kits 46, the starter kits 48, the convenience kits 50, the regular sized emergent kits 52, the compact sized emergent kits 54, the travel kits 56, and the compact kits 58, as determined by the anticipated hygienic requirements of the user.

Figure 5:
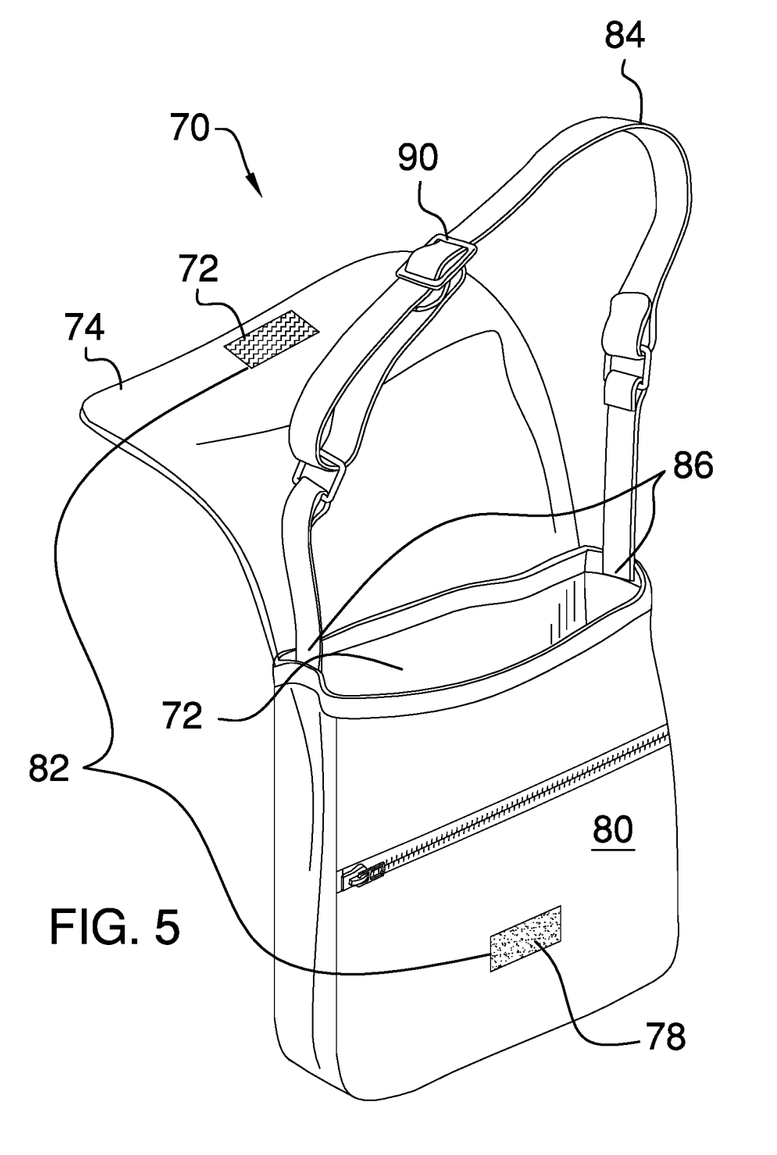
FIG. 5 is an isometric perspective view of an embodiment of the disclosure.
Figure 6:
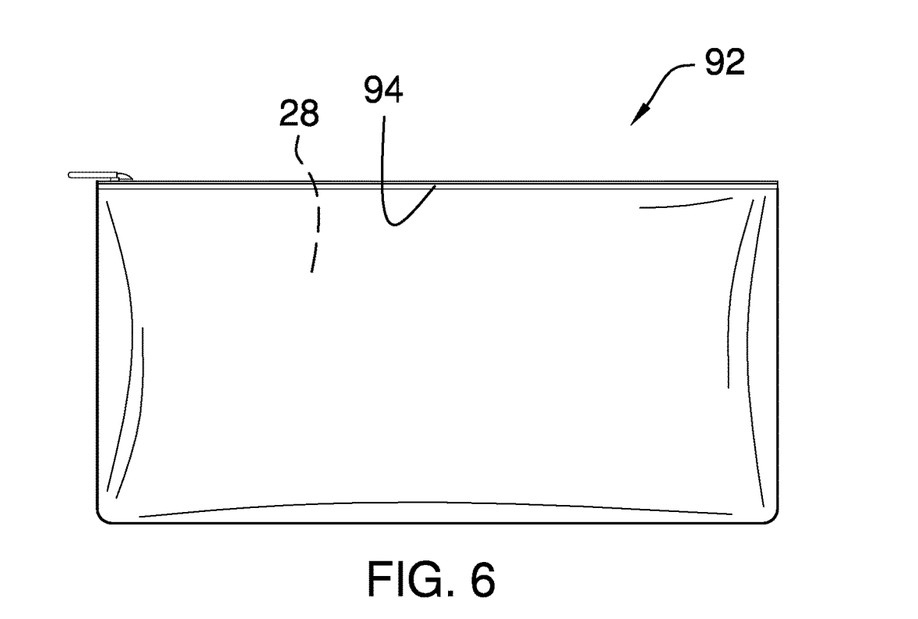
FIG. 6 is a front view of an embodiment of the disclosure.

The assembly 10 also comprises a handbag 70, shown in FIG. 5, that is sized to accommodate the car kit 68 selected by the user. The handbag 70 has a top 72 that is open so that the top 72 is positioned to insert the car kit 68 into the handbag 70. A flap 74 that is coupled to the handbag 70 proximate to the top 72 is positioned to selectively close the top 72. A first coupler 76 is coupled to the flap 74 and a second coupler 78 is coupled to a front 80 of the handbag 70. The second coupler 78 is complementary to the first coupler 76 so that the second coupler 78 is positioned to selectively couple to the first coupler 76 to fixedly position the flap 74 over the top 72. The second coupler 78 and the first coupler 76 comprises a hook and loop fastener 82.

A strap 84 with opposing ends 86 that are coupled to the handbag 70 proximate to the top 72 defines a loop 88. The loop 88 is configured to insert a respective arm of the user, positioning the strap 84 on a shoulder of the user. The strap 84 comprises a buckle 90 that is selectively couplable to the strap 84 so that the loop 88 is selectively sizable.

The assembly 10 also comprises a long pouch 92 that is sized complementarily to a plurality of tampons 28. The long pouch 92 has an upper end 94 that is zippered so that the upper end 94 is configured to be selectively opened, positioning the user to insert the plurality of tampons 28 into the long pouch 92 and to insert the long pouch 92 and the plurality of tampons 28 into a purse.

The assembly 10 also comprises a travel pouch 96 that is sized complementarily to a respective travel kit 56. The travel pouch 96 has an upper edge 98 that is zippered so that the upper edge 98 is configured to be selectively opened, positioning the user to insert the respective travel kit 56 into the travel pouch 96.

The assembly 10 also comprises a compact pouch 100 that is sized complementarily to at least one compact kit 58. The compact pouch 100 is positioned to insert the at least one compact kit 58. The compact pouch 100 comprises a side panel 102 that extends between a pair of end panels 104. The side panel 102 is zippered so that the side panel 102 is configured to be selectively opened, positioning the user to enclose the at least one compact kit 58 within the compact pouch 100. A respective end panel 104 also is zippered so that the end panel 104 is configured to be opened, positioning the user to retrieve the at least one compact kit 58 from the compact pouch 100.

In use, the master kit 12 can fulfill the hygienic requirements of the user for an extended period of time. Additionally, respective subkits 14 are available to the user, from the master kit 12, to fulfill the hygienic requirements of the user for shorter periods of time.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded.

A reference to an element by the indefinite article "a" does not exclude the possibility that more than one of the element is present, unless the context clearly requires that there be only one of the elements.

I claim:

1. A feminine hygiene product assembly comprising a master kit comprising a plurality of subkits, each subkit comprising a plurality of hygienic products, each hygienic product being positioned in an associated bag, each hygienic product having a respective function such that each subkit comprises hygienic products having a variety of functions wherein the master kit is configured for providing a user a respective subkit for addressing associated hygienic requirements of the user;
   each subkit comprising at least one of a plurality of tampons, a plurality of compact tampons, a plurality of sanitary napkins, a plurality of panty liners, a plurality of sanitary wipes, a plurality of analgesic capsules, and a plurality of analgesic tablets; and
   the plurality of subkits comprising:
      a plurality of maxicare kits, each maxicare kit comprising a plurality of sanitary napkins, each sanitary napkin have a respective absorbency such that the maxicare kit comprises sanitary napkins having a variety of absorbencies;
      a plurality of tampon kits, each tampon kit comprising a plurality of tampons, each tampon have a respective absorbency such that the tampon kit comprises tampons having a variety of absorbencies;
      a plurality of compact tampon kits, each compact tampon kit comprising a plurality of compact tampons, each compact tampon have a respective absorbency such that the compact tampon kit comprises compact tampons having a variety of absorbencies;
      a plurality of starter kits, each starter kit comprising a plurality of tampons, a plurality of panty liners, a plurality of sanitary wipes, and at least one of a plurality of analgesic capsules and a plurality of analgesic tablets;
      a plurality of convenience kits, each convenience kit comprising a plurality of tampons and plurality of sanitary wipes;
      a plurality of regular sized emergent kits, each regular sized emergent kit comprising a plurality of tampons and plurality of sanitary wipes;
      a plurality of compact sized emergent kits, each compact sized emergent kit comprising a plurality of compact tampons and plurality of sanitary wipes;
      a plurality of travel kits, each travel kit comprising a plurality of tampons a plurality of sanitary napkins, a plurality of sanitary wipes, and at least one of a plurality of analgesic capsules and a plurality of analgesic ta lets; and
      a plurality of compact kits, each compact kit comprising a plurality of compact tampons, a plurality of panty liners, a plurality of sanitary wipes, and at least one of a plurality of analgesic capsules and a plurality of analgesic tablets.

2. The assembly of claim 1, further including the associated bag being re-sealable zipper storage type.

3. The assembly of claim 1, further including the associated bag being substantially transparent such that the hygienic product is viewable through the associated bag.

4. The assembly of claim 1, further comprising:
   the maxicare kit comprising three sanitary napkins individually configured for light, regular, and overnight menstruation;
   the tampon kit comprising one each of tampons rated for light absorbency, regular absorbency, super absorbency, and super plus absorbency;
   the compact tampon kit comprising one each of compact tampons rated for light absorbency, regular absorbency, super absorbency, and super plus absorbency;
   the starter kit comprising two tampons rated for light absorbency, two panty liners, one sanitary wipe, and at least one of a pair of analgesic capsules and a pair of analgesic tablets;
   the convenience kit comprising one each of tampons rated for light absorbency, regular absorbency, super absorbency, and super plus absorbency, and one sanitary wipe;
   the regular sized emergent kit comprising one each of tampons rated for light absorbency, regular absorbency, super absorbency, and super plus absorbency, and one sanitary wipe;
   the compact sized emergent kit comprising one each of compact tampons rated for light absorbency, regular absorbency, super absorbency, and super plus absorbency, and one sanitary wipe;
   the travel kit comprising two tampons, two sanitary napkins, one sanitary wipe, and at least one of a pair of analgesic capsules and a pair of analgesic tablets; and
   the compact kit comprising three compact tampons, one panty liner, and at least one of a pair of analgesic capsules and a pair of analgesic tablets.

5. The assembly of claim 1, further including a plurality of sleeves, each hygienic product being sealable contained within a respective sleeve for maintaining sterility of the hygienic product.

6. The assembly of claim 5, further including the respective sleeve being substantially transparent such that the hygienic product is viewable through the respective sleeve.

7. The assembly of claim 5, further including a plurality of product indicia, respective product indicia being coupled to a respective sleeve for identifying an associated hygienic product positioned in the respective sleeve.

8. The assembly of claim 1, further including a plurality of kit indicia, respective kit indicia being coupled to a respective bag for identifying an associated subkit positioned in the respective bag, kit indicia comprising a date.

9. The assembly of claim 1, further including a box configured for stowing the master kit.

10. The assembly of claim 1, further including a starter pouch sized complementarily to the starter kit wherein the starter pouch is positioned for inserting the starter kit, the starter pouch comprising a sack with a cinch closure and a handle positioning the user for enclosing the starter kit within the sack and carrying the sack by the handle.

11. The assembly of claim 1, further including a car kit comprising at least one of the maxicare kits, the tampon kits, the compact tampon kits, the starter kits, the convenience kits, the regular sized emergent kits, the compact sized emergent kits, the travel kits, and the compact kits.

12. The assembly of claim 11, further comprising:
a handbag sized complementarily to the car kit, the handbag having a top, the top being open such that the top is positioned for inserting the car kit into the handbag;
a flap coupled to the handbag proximate to the top wherein the flap is positioning for selectively closing the top;
a first coupler coupled to the flap; and
a second coupler coupled to a front of the handbag, the second coupler being complementary to the first coupler wherein the second coupler is positioned for selectively coupling to the first coupler tor fixedly positioning the flap over the top, the second coupler and the first coupler comprising a hook and loop fastener.

13. The assembly of claim 12, further including a strap having opposing ends coupled to the handbag proximate to the top defining a loop wherein the loop is configured for inserting a respective arm of the user positioning the strap on a shoulder of the user, the strap comprising a buckle, the buckle being selectively couplable to the strap such that the loop is selectively sizable.

14. The assembly of claim 1, further including a long pouch sized complementarily to a plurality of tampons, the long pouch having an upper end, the upper end being zippered wherein the upper end is configured for selectively opening, positioning the user for inserting the plurality of tampons into the long pouch and for inserting the long pouch and the plurality of tampons into a purse.

15. The assembly of claim 1, further including a travel pouch sized complementarily to a respective travel kit, the travel pouch having an upper edge, the upper edge being zippered wherein the upper edge is configured for selectively opening, positioning the user for inserting the respective travel kit into the travel pouch.

16. The assembly of claim 1, further including a compact pouch sized complementarily to at least one compact kit wherein the compact pouch is positioned for inserting the at least one compact kit.

17. The assembly of claim 16, further including the compact pouch comprising a side panel extending between a pair of end panels, the side panel being zippered Wherein the side panel is configured for selectively opening, positioning the user for enclosing the at least one compact kit within the compact pouch, a respective end panel being zippered wherein the end panel is configured for opening, positioning the user tor retrieving the at least one compact kit from the compact pouch.

18. A feminine hygiene product assembly comprising:
a master kit comprising a plurality of subkits, each subkit comprising a plurality of hygienic products, each hygienic product being positioned in an associated bag, each hygienic product having a respective function such that each subkit comprises hygienic products having a variety of functions wherein the master kit is configured for providing a user a respective subkit for addressing associated hygienic requirements of the user, the associated bag being re-sealable zipper storage type, the associated bag being substantially transparent such that the hygienic product is viewable through the associated bag, each subkit comprising at least one of a plurality of tampons, a plurality of compact tampons, a plurality of sanitary napkins, a plurality of panty liners, a plurality of sanitary wipes, a plurality of analgesic capsules, and a plurality of analgesic tablets, the plurality of subkits comprising:
a plurality of maxicare kits, each maxicare kit comprising a plurality of sanitary napkins, each sanitary napkin have a respective absorbency such that the maxicare kit comprises sanitary napkins having a variety of absorbencies, the maxicare kit comprising three sanitary napkins individually configured for light, regular, and overnight menstruation,
a plurality of tampon kits, each tampon kit comprising a plurality of tampons, each tampon have a respective absorbency such that the tampon kit comprises tampons having a variety of absorbencies, the tampon kit comprising one each of tampons rated for light absorbency, regular absorbency, super absorbency, and super plus absorbency,
a plurality of compact tampon kits, each compact tampon kit comprising a plurality of compact tampons, each compact tampon have a respective absorbency such that the compact tampon kit comprises compact tampons having a variety of absorbencies, the compact tampon kit comprising one each of compact tampons rated for light absorbency, regular absorbency, super absorbency, and super plus absorbency,
a plurality of starter kits, each starter kit comprising a plurality of tampons, a plurality of panty liners, a plurality of sanitary wipes, and at least one of a plurality of analgesic capsules and a plurality of analgesic tablets, the starter kit comprising two tampons rated for light absorbency, two panty liners, one sanitary wipe, and at least one of a pair of analgesic capsules and a pair of analgesic tablets,
a plurality of convenience kits, each convenience kit comprising a plurality of tampons and plurality of sanitary wipes, the convenience kit comprising one each of tampons rated for light absorbency, regular absorbency, super absorbency, and super plus absorbency, and one sanitary wipe,
a plurality of regular sized emergent kits, each regular sized emergent kit comprising a plurality of tampons and plurality of sanitary wipes, the regular sized emergent kit comprising one each of tampons rated for light absorbency, regular absorbency, super absorbency, and super plus absorbency, and one sanitary wipe,
a plurality of compact sized emergent kits, each compact sized emergent kit comprising a plurality of compact tampons and plurality of sanitary wipes, the compact sized emergent kit comprising one each of compact tampons rated for light absorbency, regular absorbency, super absorbency, and super plus absorbency, and one sanitary wipe, a plurality of travel kits, each travel kit comprising a plurality of tampons, a plurality of sanitary napkins, a plurality of sanitary wipes, and at least one of a plurality of analgesic capsules and a plurality of analgesic tablets, the travel kit comprising two tampons, two sanitary napkins, one sanitary wipe, and at least one of a pair of analgesic capsules and a pair of analgesic tablets, and a plurality of compact kits, each compact kit comprising a plurality of compact tampons, a plurality of panty liners, a plurality of sanitary wipes, and at least one of a plurality of analgesic capsules and a plurality of analgesic tablets, the compact kit comprising three compact tampons, one panty liner, and at least one of a pair of analgesic capsules and a pair of analgesic tablets;

a plurality of sleeves, each hygienic product being sealably contained within a respective sleeve for maintaining sterility of the hygienic product, the respective sleeve being substantially transparent such that the hygienic product is viewable through the respective sleeve;

a plurality of kit indicia, respective kit indicia being coupled to a respective bag for identifying an associated subkit positioned in the respective bag, the kit indicia comprising a date;

a plurality of product indicia, respective product indicia being coupled to a respective sleeve for identifying an associated hygienic product positioned in the respective sleeve;

a box configured for stowing the master kit;

a starter pouch sized complementarily to the starter kit wherein the starter pouch is positioned for inserting the starter kit, the starter pouch comprising a sack with a cinch closure and a handle positioning the user for enclosing the starter kit within the sack and carrying the sack by the handle;

a car kit comprising at least one of the maxicare kits, the tampon kits, the compact tampon kits, the starter kits, the convenience kits, the regular sized emergent kits, the compact sized emergent kits, the travel kits, and the compact kits;

a handbag sized complementarily to the car kit, the handbag having a top, the top being open such that the top is positioned for inserting the car kit into the handbag;

a flap coupled to the handbag proximate to the top wherein the flap is positioning for selectively closing the top;

a first coupler coupled to the flap;

a second coupler coupled to a front of the handbag, the second coupler being complementary to the first coupler wherein the second coupler is positioned for selectively coupling to the first coupler for fixedly positioning the flap over the top, the second coupler and the first coupler comprising a hook and loop fastener;

a strap having opposing ends coupled to the handbag proximate to the top defining a loop wherein the loop is configured for inserting a respective arm of the user positioning the strap on a shoulder of the user, the strap comprising a buckle, the buckle being selectively couplable to the strap such that the loop is selectively sizable;

a long pouch sized complementarily to a plurality of tampons, the long pouch having an upper end, the upper end being zippered wherein the upper end is configured for selectively opening, positioning the user for inserting the plurality of tampons into the long pouch and for inserting the long pouch and the plurality of tampons into a purse;

a travel pouch sized complementarily to a respective travel kit, the travel pouch having an upper edge, the upper edge being zippered wherein the upper edge is configured for selectively opening, positioning the user for inserting the respective travel kit into the travel pouch; and a compact pouch sized complementarily to at least one compact kit wherein the compact pouch is positioned for inserting the at least one compact kit, the compact pouch comprising a side panel extending between a pair of end panels, the side panel being zippered wherein the side panel is configured for selectively opening, positioning the user for enclosing the at least one compact kit within the compact pouch, a respective end panel being zippered wherein the end panel is configured for opening, positioning the user tier retrieving the at least one compact kit from the compact pouch.

* * * * *